United States Patent [19]

Park et al.

[11] Patent Number: 4,852,388
[45] Date of Patent: Aug. 1, 1989

[54] METHOD FOR MEASURING DENSITY OF NEWTONIAN AND NON-NEWTONIAN FLUIDS

[75] Inventors: Noh-Aeok Park, Norristown, Pa.; Thomas F. Irvine, Jr., Stony Brook, N.Y.

[73] Assignee: J & L Instruments Corporation, Norristown, Pa.

[21] Appl. No.: 214,299

[22] Filed: Jul. 1, 1988

Related U.S. Application Data

[63] Continuation-in-part of Ser. No. 178,461, Apr. 7, 1988, abandoned, which is a continuation-in-part of Ser. No. 168,167, Mar. 15, 1988, abandoned.

[51] Int. Cl.$^4$ .................... G01N 9/00; G01N 11/12
[52] U.S. Cl. .................................. 73/32 R; 73/57
[58] Field of Search .................. 73/30, 32 R, 57, 444

[56] References Cited

U.S. PATENT DOCUMENTS

| | | | |
|---|---|---|---|
| 3,697,730 | 10/1972 | Clack et al. | 73/32 R |
| 3,713,327 | 1/1973 | Clemens | 73/32 R |
| 4,637,250 | 1/1987 | Irvine et al. | 73/57 |

FOREIGN PATENT DOCUMENTS 2912628 10/1980 Fed. Rep. of Germany .......... 73/57

OTHER PUBLICATIONS

Irving et al., An Automatic High Pressure Viscometer; J. Physic, vol. 4, No. 3 (Mar. 1971).
Lohrentz et al., *A. I. Ch. E. Journal*, 6, No. 4., pp. 547–549 (1960).
G. S. Smith, *J. Ins. Pet.*, 43, pp. 227–230 (1957).
Van Wazer et al., *Viscosity and Flow Measurement*, pp. 47–96, Interscience Publishers, New York, 1963.

*Primary Examiner*—Hezron E. Williams
*Attorney, Agent, or Firm*—Woodcock Washburn Kurtz Mackiewicz & Norris

[57] ABSTRACT

The present invention relates to a method for determining the density of a liquid using a falling needle viscometer. The viscometer includes a vertical cylinder which is filled with the liquid the density of which is to be determined. Using a funnel at the top of the cylinder, a first needle having a known density is allowed to fall through the liquid in the cylinder. The time that the needle falls between two marks, or transducers, spaced on the cylinder a known distance is measured from which the velocity of the needle through the liquid is calculated. Then a second needle having the same dimensions as the first and a known density different from that of the first needle is allowed to fall through the liquid. The time that the second needle falls between the two marks on the cylinder or transducers is measured and the velocity of the second needle through the liquid is calculated. Using the densities of the two needles and the velocities of the needles through the Newtonian liquid the density of the liquid is calculated using disclosed equations. Using the densities three needles and the velocities of the needles through the non-Newtonian liquid, the density of the liquid is calculated using the disclosed equations.

13 Claims, 2 Drawing Sheets

METHOD FOR MEASURING DENSITY OF NEWTONIAN AND NON-NEWTONIAN FLUIDS

RELATED APPLICATIONS

This application is a continuation-in-part of co-pending application Ser. No. 178,461, filed Apr. 7, 1988; now abandoned which is a continuation-in-part of co-pending application Ser. No. 168,167, filed Mar. 15, 1988 now abandoned.

FIELD OF THE INVENTION

The present invention relates to a method of measuring the density of Newtonian and Non-Newtonian fluids. More particularly, the present invention relates to a method of measuring the density of a fluid using a falling needle viscometer.

BACKGROUND OF THE INVENTION

A fluid can generally be classified as ideal, Newtonian or non-Newtonian based on the behavior of the fluid under stress. An ideal fluid has no shear stress in a flow field and its viscosity is zero. No fluids which exhibit this type of behavior exist. In a Newtonian fluid, such as water and glycerol, the shear stress is directly proportional to the shear rate; and its viscosity is independent of the shear rate. In a non-Newtonian fluid, the shear stress is dependent on the shear rate and its viscosity may vary with the shear rate in a complex manner.

Viscosity is a measurement of the behavior of a fluid under stress. It is therefore, important to be able to accurately determine the viscosity of a fluid in order to improve the design of pumps, stirrers, mixers, liquid transport devices, and reactors. Furthermore, the molecular weight of a polymer solution is related to its viscosity at zero shear rate and an accurate determination of the zero shear rate viscosity of a polymer solution enables one to obtain an accurate measurement of its molecular weight.

Density of a fluid is defined as its mass per unit volume. In certain instances it is desirable to determine the density of a fluid along with its viscosity under identical conditions. Density and viscosity vary with temperature and it would be desirable to determine both over a wide temperature range.

Many methods have been developed to determine the viscosity of fluids. The earliest is the capillary type viscometer in which a fluid flow is provided through a capillary tube and the drop in pressure across a length of the tube is used to determine the viscosity. This technique suffers from many disadvantages. It is difficult to accurately measure the small pressure differences involved, precisely calibrate the diameter of the capillary tube and keep the capillary tube clean. Further, the capillary tube viscometer is only applicable for determining the viscosity at high shear rates. It cannot be used to determine viscosity at low shear rates.

Another technique is the falling sphere or falling ball viscometry first described in G. G. Stokes, *Camb. Phil. Trans.*, 9, p. 8 (1851). In this method the viscosity is determined from the time taken for a sphere to fall through a predetermined distance in an infinite fluid. However, in the falling sphere method, the following assumptions are made: the spheres are falling in an infinite medium, the density of the falling sphere is in a suitable range for the equation used to determine the viscosity to hold true, and the sphere must be perfectly round, so that it will fall vertically through the fluid and will not veer in one direction or another or fall erratically.

In practice, spheres can only be made from a limited range of materials, such as, glass, aluminum or steel and the density cannot be adjusted. Further, very few spheres are truly round and, as a consequence, the fall through the fluid medium is often not vertical. Moreover, a fluid must be held in a container, therefore, wall effects have to be considered. Thus, inaccuracies arise from the non-vertical fall of a sphere and a correction factor for wall effects must be applied. Moreover, the falling sphere method does not provide an exact solution for non-Newtonian fluids because of the geometric complexities involved.

Falling cylinder and falling plunger viscometers have also been designed. See, Lohrentz, et al., *A. I. Ch. E. Journal*, 6, No. 4, p. 547–549 (1960) and G. S. Smith, *J. Inst. Pet.*, 43, p. 227–230 (1957). These are found wanting because it is difficult to construct the falling cylinder or plunger, difficult to obtain cylinders or plungers with different densities and difficult to maintain a vertical fall through the fluid. To maintain a vertical fall through the fluid, guide pins or bushings are required. Further, the eccentricity effect is very significant. Because of these problems, it is difficult to account for the systematic error in viscosity measurement by the falling cylinder or plunger method.

A rotating cylinder viscometer with two coaxial cylinders, a rotating outside cylinder and a stationary inside cylinder, has been developed to measure the viscosity of non-Newtonian fluids. See Van Wazer et al., *Viscosity and Flow Measurement*, p. 47–96, Interscience Publishers, New York, 1963. However, the rotating cylinder viscometer is difficult and expensive to make because small torque measurements on the stationary spindle are needed for compensation purposes. Further, it is very difficult to maintain a constant temperature in the system and evaporation of the fluid from the open mouth container is unavoidable. These difficulties often translate into unacceptably large errors in the viscosity obtained.

Recently, an apparatus and method for the accurate determination of the viscosity of Newtonian and non-Newtonian fluids which is simple and easy to use has been developed. That apparatus is the subject of U.S. patent application Ser. No. 697,747 filed Jan. 24, 1985, now U.S. Pat. No. 4,637,250 entitled Apparatus and Method For Viscosity Measurements For Newtonian and Non-Newtonian Fluids by the present inventors, which patent is incorporated herein by reference as if set forth in full. The apparatus includes a cylinder for holding the fluid for which the viscosity is to be determined, a needle, a funnel placed at the top of the cylinder for feeding the needle into the fluid in the cylinder, means at the bottom of the cylinder for collecting the needle, means for maintaining the cylinder and its contents at a constant temperature, and means for measuring the time of fall of the needle between two marks on the wall of the cylinder space a predetermined distance. The needle is made of tubing of a material selected from glass, aluminum or stainless steel and is capable of being adjusted in density with thin metal inserts and sealed hemispherically at both ends. The viscosity is measured by allowing the needle to fall through the liquid in the cylinder while maintaining the cylinder and its contents at a constant temperature. The time of fall of the needle between the two spaced marks on the cylinder or transducers is measured. From this measurement and the dimensions of the apparatus, the viscosity can be calculated.

For many purposes, it is also desirable to know the density of the liquid as well as its viscosity. Standard techniques for measuring density are not good for high temperature liquids since it is not possible to heat the apparatus used to measure the density to these high temperatures. Therefore, it would be desirable to be able to determine the density of the fluid, particularly at substantially the same time and with the same apparatus used to measure the viscosity of the liquid.

SUMMARY OF THE INVENTION

A method of determining the density of a Newtonian fluid includes allowing a needle of a first predetermined density to fall through the fluid in a cylinder which is maintained at a constant temperature and measuring the time of fall along a predetermined distance along the cylinder. A needle having the same length and diameter as the first needle of a second predetermined density is allowed to fall though the fluid in the cylinder while maintaining the cylinder at a constant temperature and measuring the time of fall along the predetermined distance along the cylinder. Using these measurements, the density is calculated using the following equation:

$$\rho_f = \frac{(\rho_{s1} - \rho_{s2})(V_{t1}/V_{t2})}{1 - (V_{t1}/V_{t2})} = \rho_{s1} \frac{1 - \frac{\rho_{s2}}{\rho_{s1}}(V_{t1}/V_{t2})}{1 - V_{t1}/V_{t2}}$$

where $\rho_f$ = density of liquid, $\rho_{s1}$ and $\rho_{s2}$ = densities of the two needles respectively, and $V_{t1}$ and $V_{t2}$ = velocities of the two needles respectively.

For non-Newtonian fluids three needles of different predetermined densities are utilized to determine density. First, the flow index, n, must be determined. The flow index, n, is defined as the slope of a line formed between the ln $(\rho_s - \rho_f)$ vs ln $V_t$ points for each of three needles. To find the flow index, three needles are dropped through the non-Newtonian fluid. The densities of the three needles are close enough to each other so that three points, one for each needle, plotted on a ln $(\rho_s - \rho_f)$ vs ln $V_t$ graph form a straight line. The flow index, n, is equal to the slope of that line. The following equation may also be used for determining the flow index n $$\frac{V_{t1}}{V_{t3}}^n \frac{\rho_{s2}}{\rho_{s1}} - \frac{\rho_{s3}}{\rho_{s1}} - \frac{V_{t2}}{V_{t3}}^n \left(1 - \frac{\rho_{s3}}{\rho_{s1}}\right) - \frac{\rho_{s2}}{\rho_{s1}} + 1 = 0$$

This equation may be solved for n, after which the unknown liquid density $\rho_f$ may be obtained from $$\rho_f = \rho_{s2} \frac{1 - (\rho_{s3}/\rho_{s2})(V_{t2}/V_{t3})^n}{1 - (V_{t2}/V_{t3})^n}$$

where $\rho_f$ = density of liquid, $\rho_{s1}$, $\rho_{s2}$ and $\rho_{s3}$ = densities of the three needles respectively, and $V_{t1}$, $V_{t2}$ and $V_{t3}$ = velocities of the three needles respectively.

DETAILED DESCRIPTION OF PREFERRED EMBODIMENTS

Figure 1:
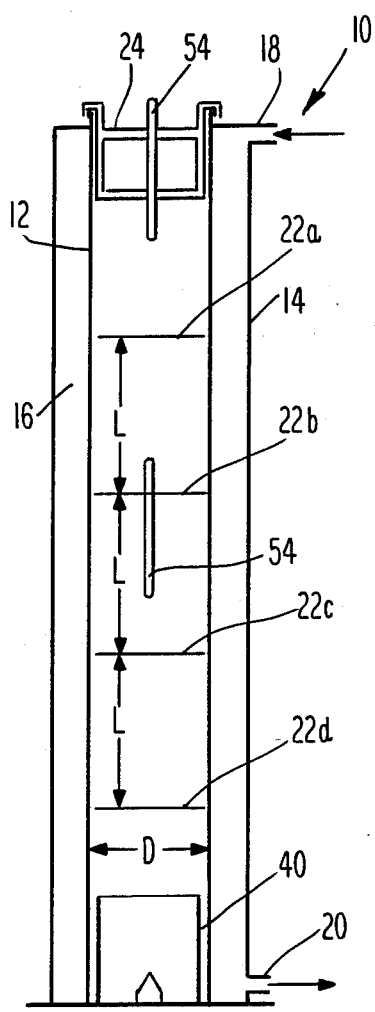
FIG. 1 is a schematic representation of a falling needle viscometer used in the method of the present invention for determining the density of a fluid.

Referring initially to FIG. 1, a falling needle viscometer used to carry out the method of the present invention is generally designated as 10. The viscometer 10 includes a cylinder 12 of internal diameter D cm., and of a transparent material, such as quartz or borosilicate glass. The cylinder 12 is filled with the liquid, i.e. the liquid whose viscosity and density are to be determined. A jacket 14, also of a transparent material, surrounds the cylinder 12 and forms a temperature control chamber 16 therebetween. The jacket 14 has an inlet 18 at one end and an outlet 20 at its other end to allow the flow of a heated or cooled liquid through the chamber 16 to maintain the cylinder 12 and its liquid contents at a constant temperature. On the wall of the cylinder 12 are a plurality of marks 22a, 22b, 22c and 22d or transducers which are spaced apart a predetermined distance L from each other along the length of the cylinder 12. In operation, a needle 54 is inserted in the top of the viscometer 10 and its velocity is determined as it passes the marks 22a, 22b, 22c and 22d. For example, the needle 54 is shown in two positions, one at the point of insertion and another as it passes mark 22b during its passage through the cylinder 12.

Figure 2:
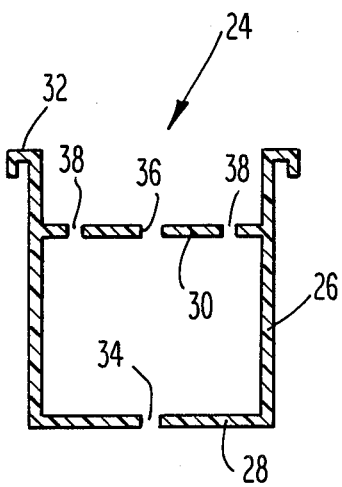
FIG. 2 is a schematic view of the funnel portion used in the viscometer shown in FIG. 1.

A funnel 24 is in the top of the cylinder 12. As shown in FIG. 2, the funnel 24 has a cylindrical outer wall 26 which fits within the cylinder 12, a bottom 28 and a spacer 30 spaced from the bottom 28. A mounting rim 32 projects radially outwardly from the top edge of the outer wall 26. The rim 32 is adapted to seat on the top edge of the cylinder 12 and thereby support the funnel 24 in the cylinder 121. The bottom 28 has a hole 34 in the center thereof which is coaxial with the vertical axis of the cylinder 12. The spacer 30 also has a center hole 36 therethrough which is aligned with the hole 34 in the bottom 28. The spacer 30 may also have additional holes 38 therethrough spaced from the center hole 36.

Figure 3:
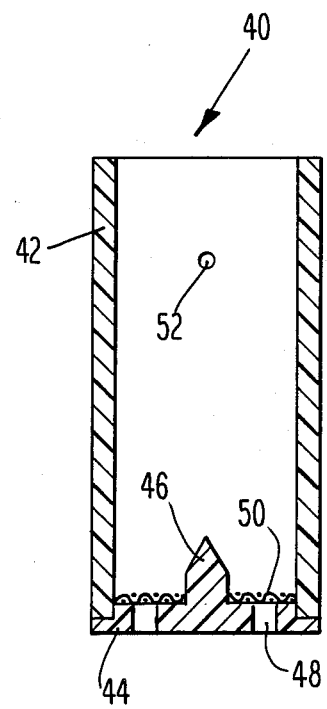
FIG. 3 is a sectional view of a collector used in the viscometer shown in FIG. 1.
Figure 4:
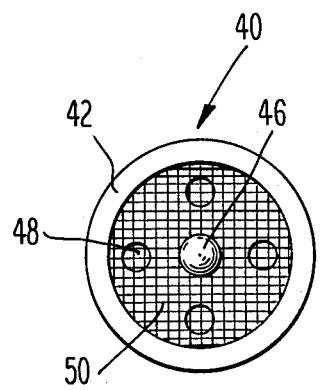
FIG. 4 is a top view of the collector.

A needle collector 40 is mounted in the bottom end of the cylinder 12 for retrieval of needles. As shown in FIGS. 3 and 4, the collector 40 has a cylindrical outer wall 42 and a bottom 44. The bottom 44 has a deflector 46 projecting upwardly from its center and a plurality of drain holes 48 therethrough around the deflector 46. A fine net 50 extends across the bottom 44 to prevent needles from falling through the drain holes 48. The outer wall 42 has a plurality of holes 52 therethrough which are adapted to receive a tool, such as a hook, for lifting the collector 40 from the cylinder 12.

Figure 5:
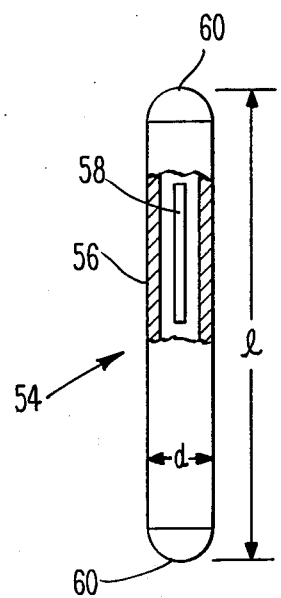
FIG. 5 is a sectional view of a needle used in the viscometer shown in FIG. 1.

As shown in FIG. 5, the needle 54 used in the viscometer 10 is formed of a tube 56 of a rigid material, such as glass, aluminum or stainless steel, having an outer diameter, d, which is no greater than 0.95 times the diameter, D, of the cylinder 12 and a length, l, which is at least 2.5 times the diameter, D, of the cylinder 12. Metal wires or weights 58 can be inserted in the needle tube 56 to adjust the density of the needle 54. After the desired density for the needle 54 is obtained by inserted an appropriate number or size of wires 58 therein, the ends of the tube 56 are sealed with heat or epoxy to provide hemispherical ends 60. It has been found that epoxy naturally forms hemispherical ends and is preferred.

To determine the density, $\rho$, of a liquid, the cylinder 12 is filled with the liquid, a collector 40 is placed in the bottom of the cylinder 12 and a funnel 24 is seated in the top of the cylinder 12. A flow of a second liquid at a desired temperature is provided through the jacket chamber 16 to bring and maintain the cylinder 12 and its contents at a constant temperature. A first needle 54 having a known density, $\rho_{s1}$, is inserted through the aligned holes 34 and 36 of the funnel 24. The needle 54 is then pushed through the holes 34 and 36 and allowed to drop through the liquid to the collector 40. As the needle falls through the cylinder 12, the time, t in sec., for the needle 54 to fall between two of the marks or transducers 22a, 22b, 22c and 22d is measured.

After the first needle 54 has fallen into the collector 40, a second needle 54 having the same dimensions as the first needle, which is adjusted by the weights 58 to have a density, $\rho_{s2}$, different from that of the first needle 54, is placed in the aligned holes 34 and 36 in the funnel 24. The second needle is then allowed to fall through the liquid in the cylinder 12 and the time, in t sec., for the second needle 54 to fall between two of the marks or transducers 22a, 22b, 22c and 22d on the cylinder 12 is measured.

For Newtonian fluids, it is known that the viscosity, u, of a Newtonian liquid can be determined using the falling needle viscometer 10 using the following equation:

$$u = \frac{g(\rho_s - \rho_f)}{V_t G}$$

where
g=gravitation constant,
$\rho_s$=density of needle,
$\rho_f$=density of fluid,
$V_t$=velocity of needle, and
G=geometric constant.

Thus, the viscosity, u, of the liquid as a function of the density $\rho_f$ may be, as determined from the velocity and density of the first needle 54 according to the following equation:

$$u_1 = \frac{g(\rho_{s1} - \rho_f)}{V_{t1} G}$$

The viscosity $u_2$ of the liquid as a function of density $\rho_f$ may be determined from the velocity and density of the second needle 54 according to the following equation:

$$u_2 = \frac{g(\rho_{s2} - \rho_f)}{V_{t2} G}$$

The viscosity of the liquid as determined by the first needle, $u_1$, and the viscosity for the liquid as determined by the second needle, $u_2$, are the same. Therefore, the foregoing equations may be divided, one by the other to yield the following:

$$\frac{u_1}{u_2} = \frac{(\rho_{s1} - \rho_f)}{(\rho_{s2} - \rho_f)} \times \frac{V_{t2}}{V_{t1}} = 1$$

A requirement of (7) is that the diameters and the lengths of the two needles are identical. If they are not identical, equation (7) must be modified to include the geometric constants. Solving equation (7) provides the following equation for determining the density of the liquid, $\rho_f$, knowing the densities of the two needles and the velocities of the two needles through the liquid:

$$\rho_f = \frac{(\rho_{s1} - \rho_{s2})(V_{t1}/V_{t2})}{1 - (V_{t1}/V_{t2})} = \rho_{s1} \frac{1 - \frac{\rho_{s2}}{\rho_{s1}}(V_{t1}/V_{t2})}{1 - V_{t1}/V_{t2}}$$

where
$\rho_f$=density of liquid,
$\rho_{s1}$ and $\rho_{s2}$=densities of the two needles respectively, and
$V_{t1}$ and $V_{t2}$=velocities of the two needles respectively.

For non-Newtonian fluids three needles of different predetermined densities, having the same length and diameters, are utilized to determine the density of the subject liquid. The densities of the three needles are close enough to each other so that points plotted on a ln $(\rho_s - \rho_f)$ vs ln $V_t$ graph for each needle form a straight line. To find the flow index, n, three needles of the type described are dropped through the non-Newtonian fluid. A point is then plotted for each needle, where each point is defined as ln $(\rho_s - \rho_f)$ vs ln $V_t$. The flow index, n, is defined as the slope of the line formed between the ln $(\rho_s = \rho_f)$ vs ln $V_t$ points for each of the three needles. The following equation may also be used for determining the flow index n, without having to plot any points:

$$\frac{V_{t1}}{V_{t3}}{}^n \frac{\rho_{s2}}{\rho_{s1}} - \frac{\rho_{s3}}{\rho_{s1}} - \frac{V_{t2}}{V_{t3}}{}^n 1 - \frac{\rho_{s3}}{\rho_{s1}} - \frac{\rho_{s2}}{\rho_{s1}} + 1 = 0$$

This equation may be solved for n, after which the unknown liquid density $\rho_f$ may be obtained from $$\rho_f = \rho_{s2} \frac{1 - (\rho_{s3}/\rho_{s2})(V_{t2}/V_{t3})^n}{1 - (V_{t2}/V_{t3})^n}$$

where
$\rho_f$=density of liquid,
$\rho_{s1}$, $\rho_{s2}$ and $\rho_{s3}$=densities of the three needles respectively, and
$V_{t1}$, $V_{t2}$ and $V_{t3}$=velocities of the three needles respectively.

Figure 6:
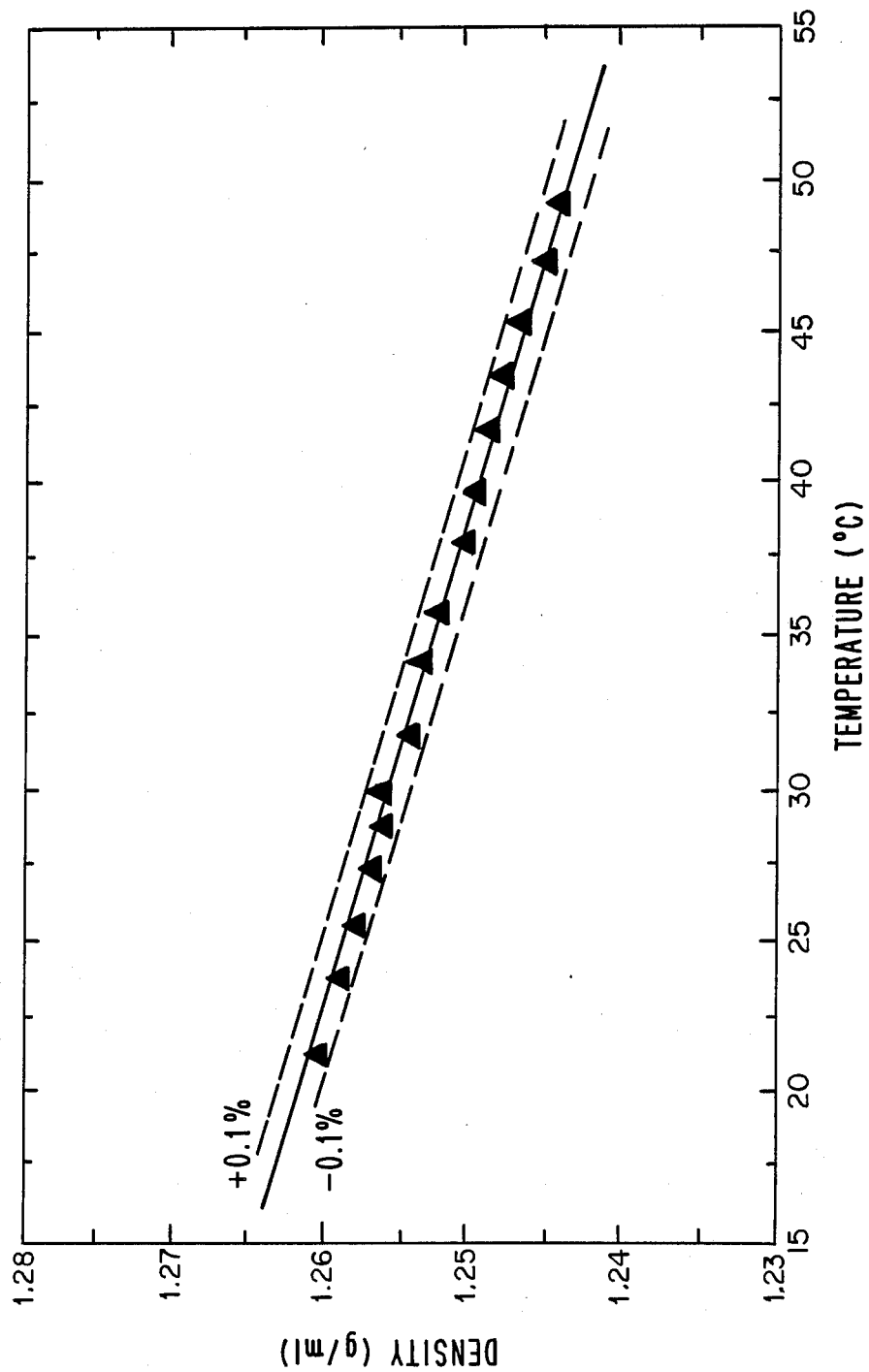
FIG. 6 is a graph of density measurements of glycerin made with the present invention showing determinations within ±0.1% of the International Critical Table values.

Referring to FIG. 6, the density of glycerol was measured at different temperatures using the present invention. The temperature was kept constant for each measurement. The density measured at each temperature is shown as a triangle. These measurements are also compared in FIG. 6 to the International Critical Table values for the density of glycerol over the same temperature range. It will be seen that measurements of density using the present invention were within ±0.1% of the International Critical Table values.

It can be seen that the density of the fluid under test $\rho_f$ may be ascertained using two falling needles in the viscometer of FIG. 1.

It may be helpful to consider how (9) was derived. For a non-Newtonian fluid the equations for determining viscosity and density differ somewhat from those used with Newtonian fluids although the general procedure employed is similar. For a non-Newtonian fluid the difference in density between needle and fluid $\rho_s - \rho_f$ are related as follows:

$$\rho_s = \rho_f = \frac{\lambda^2}{k} \frac{2Kp^{+n}}{gR^{n+1}} \frac{V_t^n}{ECF}$$

Where $\pi$ = Position of maximum fluid velocity;
$k$ = Ratio of needle to system diameter;
$K$ = Fluid consistency in power law;
$p^+$ = Dimensionless pressure in power law fluid;
$n$ = Flow index in power law fluid;
$R$ = Radius of system; and
$V_t$ = Terminal velocity
ECF = End correction factor It is apparent that n and k are constants. $\lambda$ and $p^+$ are functions of n and k and, thus the term $$\frac{\lambda^2}{k} \frac{2Kp^{+n}}{gR^{n+1}} \frac{1}{(ECF)^n}$$

is constant as well. That constant may be called A.

If three needles are used the density of each needle $\rho_{s1}$, $\rho_{s2}$ and $\rho_{s3}$ may be determined as follows:

$\rho_{s1} - \rho_f = A\, V_{t1}^n$
$\rho_{s2} - \rho_f = A\, V_{t2}^n$
$\rho_{s3} - \rho_f = A\, V_{t3}^n$ Dividing (13) by (14) yields the following:

$$\frac{\rho_{s1} - \rho_f}{\rho_{s2} - \rho_f} = \frac{V_{t1}}{V_{t2}}^n$$

Solving for $\rho_f$ $$\rho f = \frac{\rho_{s1} - \rho_{s2} \frac{V_{t1}}{V_{t2}}^n}{1 - \frac{V_{t1}}{V_{t2}}^n}$$

Dividing (14) by (15) yields the following:

$$\frac{\rho_{s2} - \rho_f}{\rho_{s3} - \rho_f} = \frac{V_{t2}}{V_{t3}}^n$$

Solving for $\rho_f$ $$\rho f = \frac{\rho_{s2} - \rho_{s3} \frac{V_{t2}}{V_{t3}}^n}{1 - \frac{V_{t2}}{V_{t3}}^n}$$

Dividing (17) by (19) yields the following:

$$\frac{V_{t1}}{V_{t3}}^n \frac{\rho_{s2}}{\rho_{s1}} - \frac{\rho_{s3}}{\rho_{s1}} - \frac{V_{t2}}{V_{t3}}^n \quad 1 - \frac{\rho_{s3}}{\rho_{s1}} - \frac{\rho_{s2}}{\rho_{s1}} + 1 = 0$$

It can be seen that (20) is identical to (2).

In the case of non-Newtonian fluids three needles are preferably employed rather than two in order to determine the trend of any change in the flow index n values.

Thus, in the method of the present invention, once the time for each needle to fall between two of the marks or transducers on the cylinder 12 is determined, the velocity of each needle can be determined by dividing the known distance between the two marks or transducers by the time. Since the density of each needle 54 is known, the density of the fluid can be determined by the above equations. Thus, there is provided by the present invention a method of easily and quickly determining the density of a fluid using a falling needle viscometer. Since the same measurement is used to determine the viscosity of the fluid, the density of the fluid can be determined at the same time as the viscosity by merely dropping a second needle through the Newtonian liquid and a second and third needle through the non-Newtonian liquid. Also, the present method can be used to measure the density of high temperature fluids since the temperature in the cylinder 12 can be easily controlled over a wide temperature range for the particular fluid.

What is claimed is:

1. A method of determining the density of a Newtonian fluid comprising the steps of:
    allowing a needle of a first predetermined density to fall through the fluid in a vertical cylinder and measuring the time of fall along a predetermined distance along the cylinder;
    allowing a needle of a second predetermined density different from the first predetermined density to fall through said fluid in the cylinder and measuring the time of fall along a predetermined distance along the cylinder; and
    calculating the density of the fluid, $\rho_f$, using the following equation:

$$\rho_f = \frac{(\rho_{s1} - \rho_{s2})(V_{t1}/V_{t2})}{1 - (V_{t1}/V_{t2})} = \rho_{s1} \frac{1 - \frac{\rho_{s2}}{\rho_{s1}}(V_{t1}/V_{t2})}{1 - V_{t1}/V_{t2}}$$

where
$\rho_{s1}$ and $\rho_{s2}$ = first and second densities of the needles respectively
$V_{t1}$ and $V_{t2}$ = velocities of the two needles respectively.

2. A method in accordance with claim 1 in which the cylinder and its contents are maintained at a constant temperature while the needles fall through the fluid.

3. A method in accordance with claim 2 in which the cylinder is maintained at a constant temperature by passing a liquid at a desired temperature through a jacket surrounding the cylinder.

4. A method in accordance with claim 2 in which the cylinder has marks thereon spaced a predetermined distance along its length and the time of fall of each needle is measured as the needles fall between said marks.

5. A method in accordance with claim 2 in which the cylinder has transducers thereon spaced a predetermined distance along its length and the time of fall of each needle is measured as the needles fall between said transducers.

6. A method in accordance with claim 4 in which the needles have a diameter no greater than 0.95 the internal diameter of the cylinder and a length at least 2.5 times the internal diameter of the cylinder.

7. A method in accordance with claim 6 in which each of the needles is a hollow tube and contains therein different metal wires to provide the needles with different densities.

8. A method in accordance with claim 7 in which the ends of the needles are sealed and are hemispherical to allow the needles to fall vertically through the liquid in the cylinder.

9. A method of determining the density of a non-Newtonian fluid comprising the steps of:
allowing a needle of a first predetermined density to fall through the fluid in a vertical cylinder and measuring the time of fall along a predetermined distance along the cylinder;
allowing a needle of a second predetermined density to fall through the fluid in a vertical cylinder and measuring the time of fall along a predetermined distance along the cylinder;
allowing a needle of a third predetermined density to fall through the fluid in a vertical cylinder and measuring the time of fall along a predetermined distance along the cylinder;
determining the flow index, n, according to the following equation:

$$\frac{V_{t1}}{V_{t3}}{}^n \frac{\rho_{s2}}{\rho_{s1}} - \frac{\rho_{s3}}{\rho_{s1}} - \frac{V_{t2}}{V_{t3}}{}^n \left[1 - \frac{\rho_{s3}}{\rho_{s1}} - \frac{\rho_{s2}}{\rho_{s1}}\right] + 1 = 0$$

determining the liquid density from following equation:

$$\rho_f = \rho_{s2} \frac{1 - (\rho_{s3}/\rho_{s2})(V_{t2}/V_{t3})^n}{1 - (V_{t2}/V_{t3})^n}$$

where
$\rho_f$ = density of liquid,
$\rho_{s1}$, $\rho_{s2}$ and $\rho_{s3}$ = densities of the three needles respectively, and
$V_{t1}$, $V_{t2}$ and $V_{t3}$ = velocities of the three needles respectively.

10. A method of claim 9 wherein the density of the needles allowed to fall through the fluid are related such that if a point is plotted for each needle on a ln $(\rho_s - \rho_f)$ vs ln $V_t$ graph, the plotted points form a straight line.

11. The method of claim 10, wherein the flow index is determined by the steps of plotting a point for each needle on a ln $(\rho_s - \rho_f)$ vs ln $V_t$ graph and thereafter determining the slope of the line passing between said points.

12. A method in accordance with claim 11 in which the needles have a diameter of no greater than 0.95 the internal diameter of the cylinder and a length of at least 2.5 times the internal diameter of the cylinder.

13. A method in accordance with claim 12 in which each of the needles is a hollow tube and contains therein different metal wires to provide the needles with different densities.

* * * * *